US00PP36082P2

(12) United States Plant Patent
van Sambeek

(10) Patent No.: US PP36,082 P2
(45) Date of Patent: Aug. 27, 2024

(54) ***AUBRIETA* PLANT NAMED 'Doaubropuim'**

(50) Latin Name: *Aubrieta gracilis*
Varietal Denomination: Doaubropuim

(71) Applicant: DUMMEN GROUP B.V., De Lier (NL)

(72) Inventor: Ellen van Sambeek, Oegstgeest (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 18/386,221

(22) Filed: Nov. 1, 2023

(51) Int. Cl.
*A01H 5/02* (2018.01)
*A01H 6/20* (2018.01)

(52) U.S. Cl.
USPC ..... Plt./263.1
CPC ..... *A01H 6/20* (2018.05)

(58) Field of Classification Search
USPC ..... Plt./263.1
CPC ..... A01H 6/20; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Aubrieta* plant named 'Doaubropuim', characterized by its compact, upright and mounding to eventually creeping plant habit; moderately vigorous growth habit; freely branching habit; dense and bushy habit; early and freely flowering habit; purple-colored flowers; and good garden performance.

2 Drawing Sheets

Figure 1:
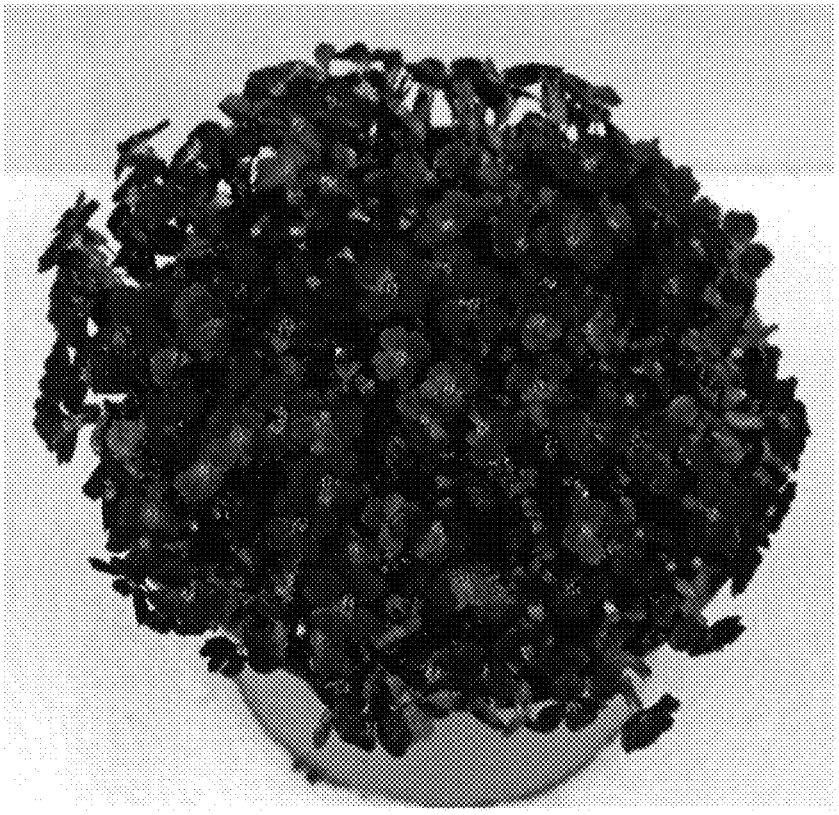

Botanical designation: *Aubrieta gracilis.*
Cultivar denomination: 'DOAUBROPUIM'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Dümmen Group B.V. of De Lier, The Netherlands on Aug. 14, 2023, application number 2023/1676. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Aubrieta* plant, botanically known as *Aubrieta gracilis*, commonly referred to as Dwarf Rock Cress and hereinafter referred to by the name 'Doaubropuim'.

The new *Aubrieta* plant is a product of a planned breeding program conducted by the Inventor in Aalsmeer, The Netherlands. The objective of the breeding program was to develop new *Aubrieta* plants with numerous attractive flowers.

The new *Aubrieta* plant originated from an open-pollination in April, 2016 in Aalsmeer, The Netherlands of a proprietary selection of *Aubrieta gracilis* identified as code number AU-0013, not patented, as the female, or seed, parent, with an unknown proprietary selection of *Aubrieta gracilis* as the male, or pollen, parent. The new *Aubrieta* plant was discovered and selected by the Inventor as a single flowering plant within the progeny of the stated open-pollination in a controlled greenhouse environment in Aalsmeer, The Netherlands in June, 2017.

Asexual reproduction of the new *Aubrieta* plant by vegetative terminal cuttings in a controlled greenhouse environment in Aalsmeer, The Netherlands since June, 2017 has shown that the unique features of this new *Aubrieta* plant are stable and reproduced true to type in successive generations.

SUMMARY OF THE INVENTION

Plants of the new *Aubrieta* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Doaubropuim'. These characteristics in combination distinguish 'Doaubropuim' as a new and distinct *Aubrieta* plant:

1. Compact, upright and mounding to eventually creeping plant habit.
2. Moderately vigorous growth habit.
3. Freely branching habit; dense and bushy habit.
4. Early and freely flowering habit.
5. Purple-colored flowers.
6. Tolerant to low and high temperatures and good garden performance.

Plants of the new *Aubrieta* differ primarily from plants of the female parent selection in flower color as flowers of plants of the new *Aubrieta* are purple in color whereas flowers of plants of the female parent selection are violet in color.

Plants of the new *Aubrieta* can also be compared to *Aubrieta gracilis* 'Kitte Blue', not patented. In side-by-side comparisons, plants of the new *Aubrieta* differ from plants of 'Kitte Blue' in the following characteristics:

1. Plants of the new *Aubrieta* flower earlier than plants of 'Kitte Blue'.
2. Plants of the new *Aubrieta* have smaller flowers than plants of 'Kitte Blue'.

BRIEF DESCRIPTION OF THE PHOTOGRAPHS

The accompanying colored photographs illustrate the overall appearance of the new *Aubrieta* plant showing the colors as true as it is reasonably possible to obtain in colored reproductions of this type. Colors in the photographs may differ slightly from the color values cited in the detailed botanical description which accurately describe the colors of the new *Aubrieta* plant.

The photograph on the first sheet (FIG. 1) is a side perspective view of a typical flowering plant of 'Doaubropuim' grown in a container.

Figure 2:
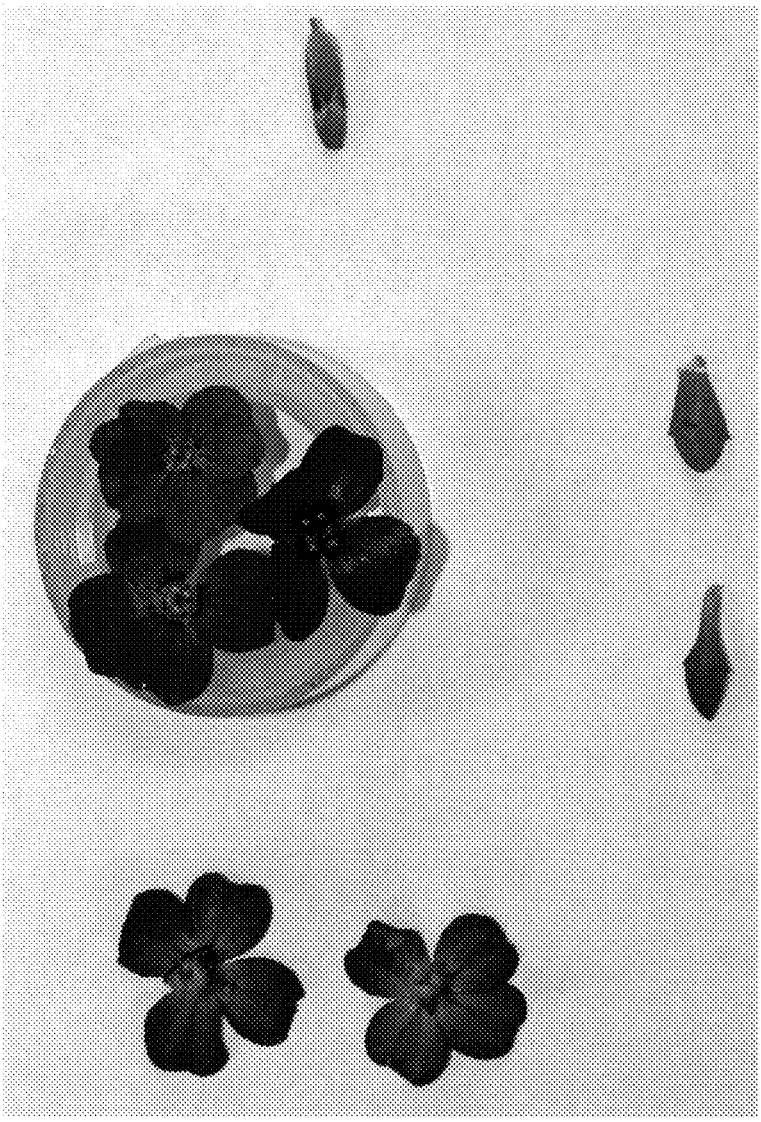

The photograph on the second sheet (FIG. 2) is a close-up view of a typical flower bud and the upper and lower surfaces of typical leaves and flowers.

DETAILED BOTANICAL DESCRIPTION

The aforementioned photographs and following observations and measurements describe plants grown during the early spring in 17-cm containers in an outdoor nursery in Aalsmeer, The Netherlands and under cultural practices typical of commercial *Aubrieta* production. During the production of the plants, average daily temperatures were 15C and average night temperatures were 4C. Plants were 35 weeks old when the photographs and description were taken. In the following description, color references are made to The Royal Horticultural Society Colour Chart, Fifth Edition, except where general terms of ordinary dictionary significance are used.

Botanical classification: *Aubrieta gracilis* 'Doaubropuim'.

Parentage:

*Female, or seed, parent.*—Proprietary selection of *Aubrieta gracilis* identified as code number AU-0013, not patented.

*Male, or pollen, parent.*—Unknown proprietary selection of *Aubrieta gracilis*, not patented.

Propagation:

*Type.*—Terminal vegetative cuttings.

*Time to initiate roots, summer.*—About 16 days at temperatures about 26C.

*Time to initiate roots, winter.*—About 21 days at temperatures about 23C.

*Time to produce a rooted young plant, summer.*—About 24 days at temperatures about 23C.

*Time to produce a rooted young plant, winter.*—About 28 days at temperatures about 18C.

*Root description.*—Medium in thickness, fibrous; typically white to light yellow in color, actual color of the roots is dependent on substrate composition, water quality, fertilizer type and formulation, substrate temperature and physiological age of roots.

*Rooting habit.*—Moderately freely branching; medium density.

Plant description:

*Plant form and growth habit.*—Perennial garden or container plant; compact, upright and mounding to eventually creeping plant habit; freely branching habit with about 160 lateral branches developing per plant; dense and bushy appearance; moderately vigorous growth habit and moderate growth rate.

*Plant height, soil level to top of foliar plane.*—About 5 cm.

*Plant height, soil level to top of floral plane.*—About 8 cm.

*Plant diameter* (*area of spread*).—About 20 cm.

*Lateral branches.*—Length: About 8 cm. Diameter: About 2 mm. Internode length: About 2 mm. Strength: Moderately strong. Aspect: Erect to about 90 degrees from vertical. Texture and luster: Smooth, glabrous; semi-glossy. Color, developing: Close to 142A. Color, developed: Close to 152C.

Leaf description:

*Arrangement.*—Opposite, decussate; simple; sessile.

*Length.*—About 1.1 cm.

*Width.*—About 5 mm.

*Shape.*—Obovate.

*Apex.*—Acute.

*Base.*—Truncate.

*Margin.*—Entire with an occasional indentation.

*Texture and luster, upper surface.*—Pubescent; glossy.

*Texture and luster, lower surface.*—Pubescent; semi-glossy.

*Venation pattern.*—Hyphodromous; single midvein discernible.

*Color.*—Developing leaves, upper surface: Close to 137B. Developing leaves, lower surface: Close to 137D. Fully developed leaves, upper surface: Close to N137A; venation, close to N137A. Fully developed leaves, lower surface: Close to 137C; venation, close to 137C.

Flower description:

*Flower type and habit.*—Rounded cruciform flowers arranged in racemes; flowers face mostly upright to outwardly; freely flowering habit, about two to three flowers per inflorescence and about 700 flowers developing per plant during the flowering season.

*Natural flowering season.*—Plants of the new *Aubrieta* begin flowering about 32 weeks after planting; plants flower continuously in the landscape for about three to four weeks in March/April in The Netherlands; flowers persistent.

*Fragrance.*—Faintly fragrant; pleasant.

*Inflorescence height.*—About 3.5 cm.

*Inflorescence diameter.*—About 2.5 cm.

*Flower diameter.*—About 2 cm.

*Flower depth* (*height*).—About 1 cm.

*Flower buds.*—Length: About 1 cm. Diameter: About 4 mm. Shape: Elliptic. Texture and luster: Smooth, glabrous; matte. Color: Close to N88A.

*Petals.*—Quantity and arrangement: Four petals arranged in a single whorl. Length: About 8 mm. Width: About 1 cm. Shape: Obcordate. Apex: Cordate. Base: Cuneate. Margin: Entire; not undulate. Texture and luster, upper and lower surfaces: Smooth, glabrous; matte. Color: When opening, upper surface: Close to N88A. When opening, lower surface: Close to N88B. Fully opened, upper surface: Close to N87A; venation, close to 83A; color does not change with subsequent development. Fully opened, lower surface: Close to N87A and N88A; venation, close to 83A; color does not change with subsequent development.

*Sepals.*—Quantity and arrangement: Four sepals arranged in a single whorl; calyx, tubular. Length: About 7 mm. Width: About 2 mm. Shape: Lanceolate. Apex: Acute. Base: Rounded. Margin: Entire. Texture and luster, upper surface: Pubescent; glossy. Texture and luster, upper surface: Smooth, glabrous; glossy. Color, when developing, upper surface: Close to 146A tinged with close to 187A. Color, when developing, lower surface: Close to 146A. Color, fully developed, upper surface: Close to 146A slightly tinged with close to 187A. Color, fully developed, lower surface: Close to 146A.

*Pedicels.*—Length: About 1.1 cm. Width: About 1 mm. Strength: Flexible, weak. Aspect: About 40 degrees from vertical. Texture and luster: Pubescent; glossy. Color: Close to 144C.

*Reproductive organs.*—Stamens: Quantity per flower: Six. Filament length: About 9 mm. Filament color: Close to NN155A. Anther size: About 0.1 mm by 1 mm. Anther color: Close to 4B. Pollen amount: Moderate. Pollen color: Close to 4B. Pistils: Quantity per flower: One. Pistil length: About 6 mm. Style length: About 2 mm. Style color: Close to 142A. Stigma diameter: About 0.5 mm. Stigma shape: Rounded, capitate. Stigma color: Close to 142A. Ovary color: Close to 142A.

*Seeds/fruits.*—To date, seed and fruit development has not been observed on plants of the new *Aubrieta.*

Pathogen & pest resistance: To date, plants of the new *Aubrieta* have not been noted to be resistant to pathogens or pests common to *Aubrieta* plants.

Garden performance: Plants of the new *Aubrieta* have been observed to have good garden performance and to tolerate temperatures ranging from about −35C to about 35C and are hardy to U.S.D.A. Hardiness Zone 4.

It is claimed:

1. A new and distinct *Aubrieta* plant named 'Doaubropuim' as illustrated and described.

* * * * *